United States Patent
Piccirilli et al.

(10) Patent No.: US 6,733,795 B2
(45) Date of Patent: May 11, 2004

(54) METHOD FOR PRODUCING AN AVOCADO LEAF EXTRACT RICH IN FURANIC LIPIDS

(75) Inventors: Antoine Piccirilli, Versailles (FR); Jacques Legrand, Neuilly sur Eure (FR)

(73) Assignee: Laboratoires Expanscience, Courbevoie (FR)

( * ) Notice: Subject to any disclaimer, the term of this patent is extended or adjusted under 35 U.S.C. 154(b) by 0 days.

(21) Appl. No.: 10/206,995

(22) Filed: Jul. 30, 2002

(65) Prior Publication Data

US 2004/0022882 A1 Feb. 5, 2004

(51) Int. Cl.$^7$ .............................................. A61K 35/78
(52) U.S. Cl. ........................ 424/725; 424/769; 424/774
(58) Field of Search ................................ 424/725, 769, 424/774

(56) References Cited

U.S. PATENT DOCUMENTS 6,133,313 A * 10/2000 Thomson et al.

OTHER PUBLICATIONS

Oelrichs et al. (Toxic Plants and other Natural Toxicants, [Proceedings of the International Symposium on Poisonous Plants], 5th, San Angelo, Tex., May 18–23, 1997 (1998), Meeting Date 1997, pp. 86–90).*

M. Farines, et al., "Influence of Avocado Oil Procesing on the Nature of Some Unsaponifable Constituents", JAOCS, 1995, pp. 473 –476, vol. 72, No. 4, ©1995 by AOCS Press.

* cited by examiner

Primary Examiner—Leon B. Lankford, Jr.
Assistant Examiner—Susan D. Coe
(74) Attorney, Agent, or Firm—Foley and Lardner

(57) ABSTRACT

The present invention relates to a method for producing an avocado leaf extract rich in furanic lipids, the raw material for which consists of avocado leaves, and which comprises the following steps: a liquid-solid extraction step followed by evaporation under vacuum, and a heat treatment step between 80 and 120° C. which is continued for a period of between 5 and 72 hours, it being possible for these two steps to be carried out in this order or in the reverse order.

20 Claims, No Drawings

METHOD FOR PRODUCING AN AVOCADO LEAF EXTRACT RICH IN FURANIC LIPIDS

The present invention relates to a method for producing an avocado leaf plant extract rich in furanic lipids.

Avocado comprises, in a known manner, particular lipids of the furan type, whose main component is a linoleic furan:

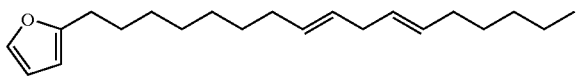

Thus, the expression "avocado furanic lipids" is understood to mean according to the invention the components corresponding to the formula:

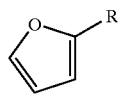

in which R is a linear $C_{11}$–$C_{19}$, preferably $C_{13}$–$C_{17}$, hydrocarbon chain which is saturated or which comprises one or more ethylenic or acetylenic unsaturations. These avocado furanic lipids have been described in particular in Farines, M et al, 1995, *J. of Am. Oil Chem. Soc.* 72, 473.

Currently, the known routes of synthesis for producing furanic lipids and the routes commonly used starting from avocados in the form of fruits as raw material.

Given the therapeutic value of avocado furanic lipids for their beneficial and curative action on the connective tissue, in particular in inflammatory pathologies such as osteoarthritis, periodontitis and scleroderma, and their high cost in general, a strong interest therefore exists in finding alternative routes for preparing these avocado furanic lipids.

The Applicant has thus developed a method which makes it possible to obtain an avocado leaf plant extract rich in furanic lipids, namely having a content ranging from 20 to 80%, and preferably 30 to 50%.

This method, in which the raw material consists of avocado leaves, comprises the following steps:
- a liquid-solid extraction step followed by evaporation under vacuum, and
- a heat treatment step between 80 and 120° C.

These two steps may be carried out in this order or in the reverse order.

The avocado leaves may be obtained from avocado plants belonging to the following varieties: Hass, Fuerte, Ettinger, Bacon, Nabal, Anaheim, Lula, Reed, Zutano, Queen, Criola Selva, Mexicana Canta, Region Dschang, Hall, Booth, Peterson, Collinson Red or Alpha Krome and more particularly to the varieties Hass, Fuerte and Reed.

Several solvents may be used during the step of liquid-solid extraction of the leaves, having previously been optionally subjected to dehydration. The solvents may be chosen from the group consisting of alkanes, halogenated alkanes, ethers, esters, alcohols, aromatic compounds and supercritical fluids. Hexane, ethanol, methanol, chloroform, dichloromethane and ethyl acetate are preferred, alone or in the form of a mixture.

The heat treatment step, whether it takes place directly on the leaves or at the plant extract stage, is carried out at temperatures of between 80 and 120° C. This heat treatment may last from 5 to 72 hours.

According to the method of the invention, the heat treatment step may be performed in the presence or otherwise of an acid catalyst.

The expression acid catalysts is understood to mean in a broad sense so-called homogeneous inorganic or organic catalysts such as hydrochloric, sulphuric, acetic or para-toluenesulphonic acids, but also, and preferably, heterogeneous solid catalysts such as silica, alumina, silicas-aluminas, zirconias, zeolites and acidic resins. Acidic aluminas with large specific surface areas, that is to say at least equal to 200 m²/g, will be chosen in particular.

The method may also comprise a step, prior to the liquid-solid extraction, of dehydration of avocado leaves.

The expression dehydration of the avocado leaves is understood to mean more generally all the techniques known to persons skilled in the art which make it possible to extract water from a compound. Among these techniques, there may be mentioned drying under a hot air stream or under a controlled atmosphere (e.g. nitrogen) at atmospheric pressure or under vacuum, in a thick layer or in a thin layer, but also microwave drying, spray-drying, freeze-drying and osmotic dehydration in solution (direct osmosis) or in solid phase (e.g. drying in osmotic bags).

In general, the temperature during this dehydration step will be preferably maintained, whatever the technique used, at less than or equal to 80° C.

Moreover, it is preferable, in the context of the present invention, to stop the dehydration when the residual moisture reaches the level of 5%.

In the context of the present invention, for the sake of ease of industrial implementation and for cost considerations, drying in ventilated dryers, in a thin layer and under a hot air stream, at a temperature of between 70 and 75° C. is preferred. The duration of the operation may vary from 5 to 72 hours.

According to a first variant, the method is carried out according to the succession of steps below:
- Step 1: heat treatment of the avocado leaves,
- Step 2: liquid-solid extraction of the avocado leaves,
- Step 3: vacuum evaporation of the solvent until a solvent-free plant extract is obtained.

According to a second variant, the method is carried out according to the succession of steps below:
- Step 1: liquid-solid extraction of the avocado leaves,
- Step 2: vacuum evaporation of the solvent until a solvent-free plant extract is obtained,
- Step 3: heat treatment of the plant extract.

According to final variant, the method is carried out according to the succession of steps below:
- Step 1: dehydration of the avocado leaves,
- Step 2: liquid-solid extraction of the avocado leaves,
- Step 3: vacuum evaporation of the solvent until a plant extract is obtained,
- Step 4: heat treatment of the plant extract.

The leaves are advantageously ground before any operation performed in the context of the method according to the invention.

The present invention finally relates to an avocado leaf plant extract which can be obtained by the method according to the invention, including according to all its variants.

The following non-limiting examples illustrate the invention.

EXAMPLE 1

One kilogram of leaves of avocado plant of the Hass variety is carefully ground. The ground product obtained (320 g) is brought into contact with 2 liters of ethanol and then heated under reflux for 5 hours. Once cool, the mixture is filtered on a Büchner funnel and the cake is washed with three times 100 ml of ethanol. The solvent is then evaporated under vacuum using a rotary evaporator, and then drawn off under vacuum for a further one hour after complete removal of the solvent. The extract obtained is then placed in an oven at 100° C. for 24 hours, and then analysed. 23 g of extract are obtained according to this method.

The physicochemical and chromatographic analyses of this extract gave the following results:
  incineration residue: <0.1%
  content of volatile compounds: <0.1%
  content of furanic lipids: 42%

EXAMPLE 2

One kilogram of leaves of avocado plant of the Fuerte variety is carefully ground. The ground product obtained (305 g) is brought into contact with 2 liters of hexane and then heated under reflux for 5 hours. Once cool, the mixture is filtered on a Büchner funnel and the cake is washed with three times 100 ml of hexane. Once assembled, the hexane-containing phases are dried in the presence of $Na_2SO_4$. The hexane is then evaporated under vacuum using a rotary evaporator, and then drawn off under vacuum for a further one hour after complete removal of the solvent. The extract obtained is then placed in an oven at 100° C. for 24 hours, and then analysed. 26 g of extract are obtained according to this method.

The physicochemical and chromatographic analyses of this extract gave the following results:
  incineration residue: <0.1%
  content of volatile compounds: <0.1%
  content of furanic lipids: 46%

EXAMPLE 3

One kilogram of leaves of avocado plant of the Hass variety is carefully ground. The ground product is brought into contact, with stirring, for 5 hours, with 10 liters of methanol, 10 liters of chloroform and 10 liters of salt water (containing 1% of NaCl). The mixture is then centrifuged and the solid pellet removed. The bottom liquid phase is recovered and then dried over $Na_2SO_4$. The solvents are then evaporated under vacuum using a rotary evaporator, and then drawn off under vacuum for a further one hour after complete removal of the solvents. The extract obtained is then placed in an oven at 100° C. for 24 hours, and then analysed. 21 g of extract are obtained according to this method.

The physicochemical and chromatographic analyses of this extract gave the following results:
  incineration residue: <0.1%
  content of volatile compounds: <0.1%
  content of furanic lipids: 46%

EXAMPLE 4

One kilogram of leaves of avocado plant of the Hass variety is carefully ground. The ground product is then dried in an oven, under a hot air stream, at 110° C. for 24 hours. 302 g of dry matter are then recovered. The latter is then brought into contact with 2 liters of hexane and then heated under reflux for 5 hours. Once cool, the mixture is filtered on a Büchner funnel and the cake is washed with three times 100 ml of hexane. The hexane is then evaporated under vacuum using a rotary evaporator, and then drawn off under vacuum for a further one hour after complete removal of the solvent. 31 g of extract are obtained according to this method.

The physicochemical and chromatographic analyses of this extract gave the following results:
  incineration residue: <0.1%
  content of volatile compounds: <0.1%
  content of furanic lipids: 41%

EXAMPLE 5

One kilogram of leaves of avocado plant of the Hass variety is carefully ground. The ground product is then dried in an oven, under a hot air stream, at 70° C. for 72 hours. 315 g of dry matter are then recovered. The residual moisture present in the leaves is then 4.8%. This dehydrated material is then brought into contact with 2 liters of hexane and then heated under reflux for 5 hours. Once cool, the mixture is filtered on a Büchner funnel and the cake is washed with three times 100 ml of hexane. The hexane is then evaporated under vacuum using a rotary evaporator, and then drawn off under vacuum for a further one hour after complete removal of the solvent. The extract obtained is then placed in an oven at 100° C. for 24 hours, and then analysed. 23 g of extract are thus obtained according to this method.

The physicochemical and chromatographic analyses of this extract gave the following results:
  incineration residue: <0.1%
  content of volatile compounds: <0.1%
  content of furanic lipids: 38%

COMPARATIVE EXAMPLE/METHOD WITHOUT EXCESSIVE HEATING OF THE LEAVES

Example: one kilogram of leaves of avocado plant of the Hass variety is carefully ground. The ground product is then dried in an oven, under a hot air stream, at 60° C. for 96 hours. 307 g of dry matter are then recovered. The latter is then brought into contact with 2 liters of hexane and then heated under reflux for 5 hours. Once cool, the mixture is filtered on a Büchner funnel and the cake is washed with three times 100 ml of hexane. The hexane is then evaporated under vacuum using a rotary evaporator, at 60° C., and then drawn off under vacuum for a further one hour after complete removal of the solvent. 27 g of extract are obtained according to this method.

The physicochemical and chromatographic analyses of this extract gave the following results:
  incineration residue: <0.1%
  content of volatile compounds: <0.1%
  content of furanic lipids: 2%

Conclusion: in the absence of extensive heating of the leaves, or of the plant extract obtained from the fresh or dehydrated leaves by a solvent extraction, the final extract obtained contains practically no furanic lipids (content considerably less than 5%).

We claim:

1. A method for producing a plant extract comprising 20 to 80% furanic lipids, wherein the raw material consists of avocado leaves and the method comprising:
   exposing leaves to a solvent in a liquid-solid extraction step followed by evaporation under vacuum, and
   a heat treatment step between 80° C. and 120° C. for a period of time,
it being possible for these two steps to be carried out in this order or in the reverse order.

2. The method of claim 1 for producing a plant extract comprising 20 to 80% furanic lipids, wherein the avocado leaves are obtained from avocado plants belonging to the following varieties: Hass, Fuerte, Ettinger, Bacon, Nabal, Anaheim, Lula, Reed, Zutano, Queen, Criola Selva, Mexicana Canta, Region Dschang, Hall, Booth, Peterson, Collinson Red or Alpha Krome.

3. The method of claim 1 for producing a plant extract comprising 20 to 80% furanic lipids, wherein the heat treatment is carried for a period varying between 5 and 72 hours.

4. The method of claim 1 for producing a plant extract comprising 20 to 80% furanic lipids, wherein the appropriate solvent or solvents during the liquid-solid extraction step are chosen from the group consisting of alkanes, halogenated alkanes, ethers, esters, alcohols, aromatic compounds and supercritical fluids.

5. The method of claim 1 for producing a plant extract comprising 20 to 80% furanic lipids, wherein the appropriate solvent or solvents during the liquid-solid extraction step are selected from the group consisting of hexane, ethanol, methanol, chloroform, dichloromethane, and ethyl acetate, taken alone or in the form of a mixture.

6. A method for producing a plant extract comprising 20 to 80% furanic lipids, the method comprising:

Step 1: dehydrating avocado leaves,

Step 2: liquid-solid extracting of said avocado leaves using a solvent,

Step 3: vacuum evaporating said solvent until a plant extract is obtained,

Step 4: heat treating said plant extract at a temperature between 80° C. and 120° C.

7. Plant extract of avocado leaves which is obtained by the method of claim 1.

8. The method of claim 1 wherein said heat treating step is performed in the presence of an acid catalyst.

9. The method of claim 1 where said leaves are ground before any step in the described method is performed.

10. The method of claim 6 where said dehydrating step is performed at a temperature that is less than or equal to 80° C.

11. The method of claim 6 where said dehydrating step is stopped when the residual moisture reaches the level of 5%.

12. The method of claim 6 where said leaves are ground before any step in the described method is performed.

13. The method of claim 6 where said heat treating step is performed in the presence of an acid catalyst.

14. The method of claim 6 for producing a plant extract comprising 20 to 80% furanic lipids, wherein the avocado leaves are obtained from avocado plants belonging to the following varieties: Hass, Fuerte, Ettinger, Bacon, Nabal, Anaheim, Lula, Reed, Zutano, Queen, Criola Selva, Mexicana Canta, Region Dschang, Hall, Booth, Peterson, Collinson Red or Alpha Krome.

15. The method of claim 6 for producing a plant extract comprising 20 to 80% furanic lipids, wherein the heat treatment is carried for a period varying between 5 and 72 hours.

16. The method of claim 6 for producing a plant extract comprising 20 to 80% furanic lipids, wherein the appropriate solvent or solvents during the liquid-solid extraction step are chosen from the group consisting of alkanes, halogenated alkanes, ethers, esters, alcohols, aromatic compounds and supercritical fluids.

17. The method of claim 6 for producing a plant extract comprising 20 to 80% furanic lipids, wherein the appropriate solvent or solvents during the liquid-solid extraction step are chosen from the group consisting of hexane, ethanol, methanol, chloroform, dichloromethane, and ethyl acetate, taken alone or in the form of a mixture.

18. The method of claim 6 for producing a plant extract comprising 20 to 80% furanic lipids, wherein the dehydration is selected from the group consisting of drying under a heated air stream, drying under a controlled atmosphere, drying at atmospheric pressure under vacuum, drying the avacado leaves in a layer, microwave drying, spray-drying, freeze-drying, and osmotic dehydration in solution and osmotic dehydration in solid phase.

19. The method of claim 6 for producing a plant extract comprising 20 to 80% furanic lipids, wherein the dehydration consists in drying the avacado leaves in ventilated dryers, in a layer of the avacado leaves and under a hot air stream, at a temperature between 70° C. and 75° C.

20. Plant extract of avocado leaves which is obtained by the method according to claim 6.

* * * * *